United States Patent [19]

Spector

[11] Patent Number: 4,535,935
[45] Date of Patent: Aug. 20, 1985

[54] RECHARGEABLE SACHET

[76] Inventor: Donald Spector, 380 Mountain Rd., Union City, N.J. 07087

[21] Appl. No.: 541,436

[22] Filed: Oct. 13, 1983

[51] Int. Cl.$^3$ ............................................. A61L 9/04
[52] U.S. Cl. ..................................... 239/34; 239/211
[58] Field of Search ................... 239/44, 45, 51.5, 34, 239/211

[56] References Cited

U.S. PATENT DOCUMENTS

| | | | |
|---|---|---|---|
| 502,544 | 8/1893 | Woodcock et al. | 239/45 |
| 1,660,085 | 2/1928 | Elnain née Nassau | 239/211 |
| 2,243,752 | 5/1941 | Dunaway | 239/44 |
| 2,586,179 | 2/1952 | Rooch | 239/51.5 |
| 3,330,481 | 7/1967 | Dearling | 239/44 |
| 3,679,133 | 7/1972 | Sekiguchi et al. | 239/34 |
| 4,346,059 | 8/1982 | Spector | 239/34 |

FOREIGN PATENT DOCUMENTS

| | | | |
|---|---|---|---|
| 70104 | 10/1949 | Denmark | 239/211 |
| 18878 | 7/1971 | Japan | 239/44 |

*Primary Examiner*—Andres Kashnikow
*Assistant Examiner*—Michael J. Forman
*Attorney, Agent, or Firm*—Michael Ebert

[57] ABSTRACT

A rechargeable sachet for scenting articles of apparel, the sachet being in a snake-like form so that it may be coiled or knotted about a post or rod in a clothes closet, or placed in a drawer in any desired shape. The sachet includes a permeable fabric sleeve having stuffed therein a flexible core of absorbent material having wicking properties. Within one end of the sleeve is a non-permeable socket which receives the corresponding end of the core, the base of the socket being provided with a projecting plug having an axial bore therein from which is extended a dip tube. The plug is inserted into the mouth of a squeeze bottle containing a reserve supply of liquid fragrance. The core is initially impregnated with a charge of the same liquid fragrance which, as it evaporates, is diffused through the sleeve into the closet or drawer to scent the clothing housed therein. When this initial charge is dissipated, the core may be recharged by squeezing the bottle end of the sleeve to inject liquid fragrance into the core end, the liquid being then wicked throughout the body of the core.

8 Claims, 5 Drawing Figures

U.S. Patent  Aug. 20, 1985  4,535,935
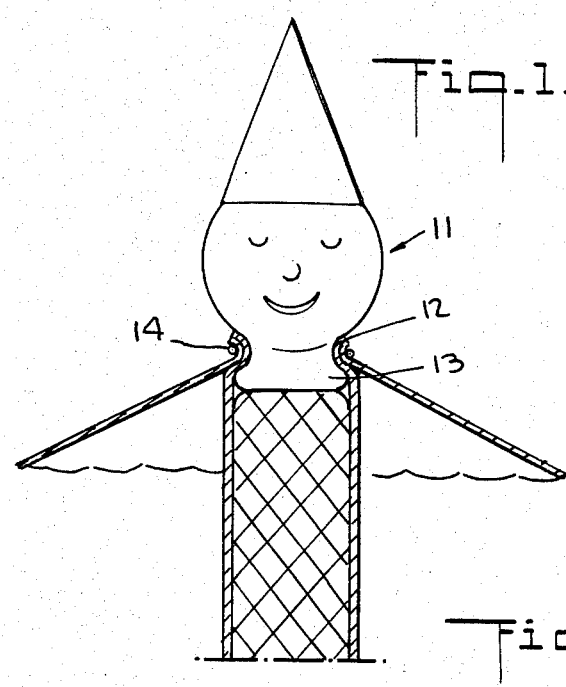
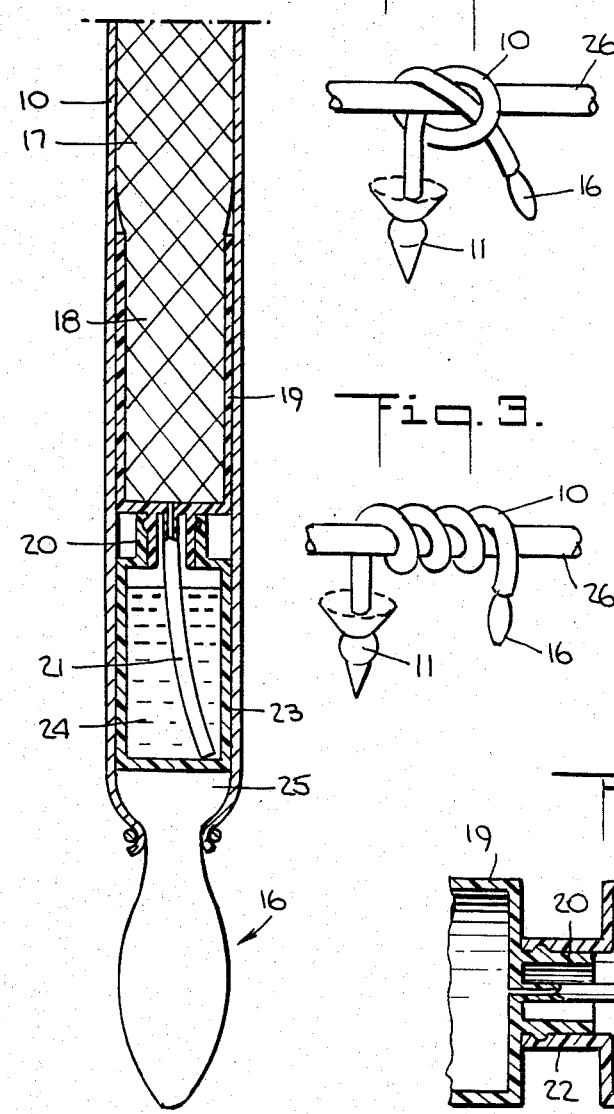
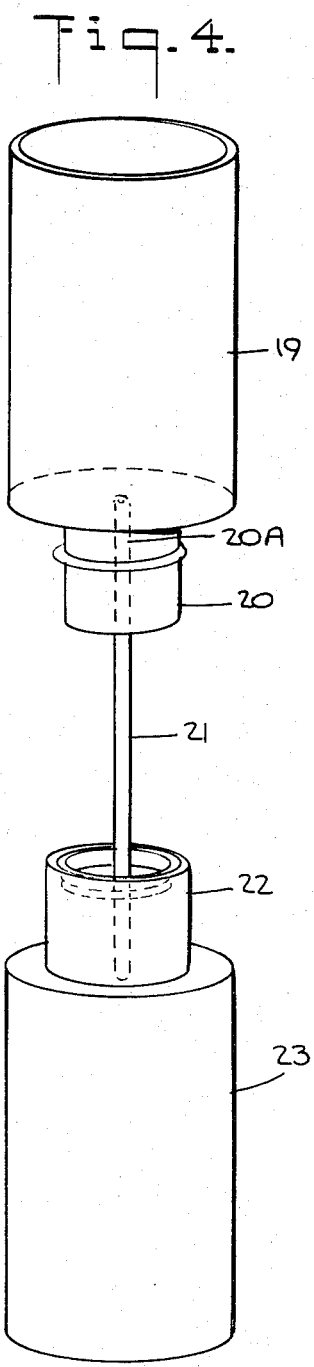
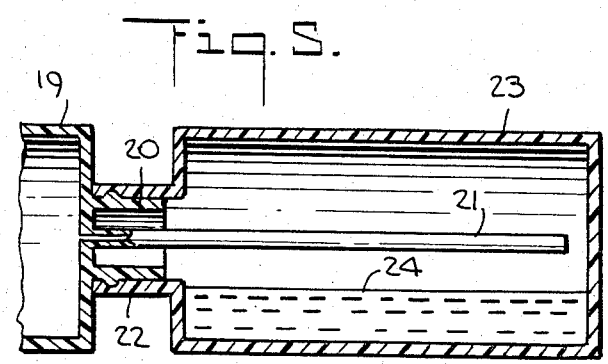

RECHARGEABLE SACHET

BACKGROUND OF INVENTION

This invention relates generally to sachets for scenting articles of apparel, and in particular to a rechargeable sachet having a snake-like form which may be coiled or knotted about a post and otherwise shaped in a manner appropriate to the placement of the sachet.

The standard sachet is constituted by a small fabric bag or pouch containing a perfumed powder. By placing this sachet in a clothes closet or in a drawer, the fragrance emitted thereby is caused to permeate the clothing and impart a pleasant scent thereto. This serves to mask the musty odor that may result from prolonged storage of clothing in an unventilated closet or drawer.

Conventional sachets, because they include a perfumed powder, tend to emit a fairly weak scent which may be insufficient to impart a distinctive fragrance to clothing exposed thereto. Moreover, such sachets have a limited life; for once the perfume is exhausted, the bag serves no useful purpose and must be discarded. And because the ordinary sachet has a bag-like form which is generally utilitarian in appearance and unappealing, its presence in a closet or drawer housing attractive articles of apparel strikes a discordant note.

In the present invention, use is made of a liquid fragrance to generate the desired scent. Perfumes and perfume-based products such as colognes and toilet waters were originally derived from the essential oils of plants. However, since early in the 19th century, chemists have succeeded in analyzing these oils and in creating thousands of synthetics, some simulating natural fragrances and others yielding altogether new scents.

Modern perfumes are mostly blends of natural and synthetic scents and fixatives which equalize vaporization and enhance pungency, the ingredients usually being combined with alcohol. A sachet in accordance with the invention is usable with any known form of liquid fragrance in any desired concentration.

SUMMARY OF INVENTION

In view of the foregoing, the main object of this invention is to provide a sachet in which a flexible core of absorbable material is impregnated with a liquid fragrance, the core having wicking properties so that the entire body of the core is permeated with the liquid to afford a relatively large scent-radiating surface.

More particularly, an object of this invention is to provide a sachet of the above type which is rechargeable, a recharge being effected simply by squeezing the sachet.

Also an object of the invention is to provide a rechargeable sachet which takes a snake-like form so that it may be knotted or coiled about a post or rod in a clothes closet at a convenient position therein, or it may be shaped for effective placement in a drawer to scent articles of clothing.

Yet another object of the invention is to provide a rechargeable sachet whose structure lends itself to decorative forms which disguise its true function, thereby obviating the utilitarian and unattractive aspects of conventional sachets.

Briefly stated, these objects are attained in a rechargeable sachet for scenting articles of apparel, the sachet being in a snake-like form so that it may be coiled or knotted about a post or rod in a clothes closet, or placed in a drawer in any desired shape. The sachet includes a permeable fabric sleeve having stuffed therein a flexible core of absorbent material having wicking properties. Within one end of the sleeve is a non-permeable socket which receives the corresponding end of the core, the base of the socket being provided with a projecting plug having an axial bore therein from which is extended a dip tube. The plug is inserted into the mouth of a squeeze bottle containing a reserve supply of liquid fragrance. The core is initially impregnated with a charge of the same liquid fragrance which, as it evaporates, is diffused through the sleeve into the closet or drawer to scent the clothing housed therein. When this initial charge is dissipated, the core may be recharged by squeezing the bottle end of the sleeve to inject liquid fragrance into the core end, the liquid being then wicked throughout the body of the core.

OUTLINE OF DRAWINGS

For a better understanding of the invention as well as other objects and further features thereof, reference is made to the following detailed description to be read in conjunction with the accompanying drawings, wherein:

FIG. 1 illustrates, partly in section, a snake-like rechargeable sachet according to the invention;

FIG. 2 shows the sachet knotted about a rod;

FIG. 3 shows the sachet coiled about a rod;

FIG. 4 separately shows the squeezable bottle and its associated socket; and

FIG. 5 shows the bottle in a horizontal position.

DESCRIPTION OF INVENTION

Referring now to the figures of the drawing, one preferred embodiment of a rechargeable sachet in accordance with the invention has a snake-like form and includes an elongated sleeve 10 fabricated of a permeable textile material such as velveteen, a fabric usually woven of cotton and made with a short, close weft pile in imitation of velvet. In practice, the sleeve may be made of any suitable natural or synthetic material which is permeable to vapor.

Attached to the upper end of sleeve 10 is a decorative headpiece 11 whose head section may represent a clown or any other human or animal figurine. This piece is molded or otherwise fabricated of ceramic, plastic or any other rigid or semi-rigid material. Integral with the head section of the headpiece is a constricted neck section 12 and a circular pedestal 13 whose diameter is close to that of the sleeve so that it may be telescoped within the sleeve to leave only the head section exposed.

The upper end of sleeve 10 is tied to headpiece 11 by an elastic ring 14 or similar means which encircles neck 12. Ring 14 also serves to secure to the sleeve a decorative fabric skirt 15 or other means which are decoratively related to the headpiece.

Similarly attached to the lower end of sleeve 10 is a rigid tail or foot piece 16 of a material that preferably matches that of the headpiece. The foot piece has a similar neck section and pedestal so that it may be telescoped within the lower end of the sleeve and secured thereto to an elastic ring or other means. The use of the terms "upper and lower" are with respect to the sachet as shown vertically, bearing in mind that in practice when the sachet is placed, it is unlikely to be vertically oriented.

The function of the headpiece and the foot or tail piece at the opposing ends of the sleeve is not purely decorative, for these pieces also serve as handles so that the user may manipulate the snake-like form and knot, coil or curve the sachet in any desired manner.

The head and foot pieces illustrated represent only one example of the various forms these pieces may take. Thus an alternative set could have as a headpiece the head of a snake and the tail piece as the rattler end thereof, in which case the fabric sleeve may take the form of a fabric having printed thereon a pattern representing snake skin.

Stuffed within sleeve 10 is a flexible core 17 of absorbent material having wicking properties. For this purpose, one may use cotton batting or other soft fibrous material. Use is also made of an open-mesh net 18 to confine and somewhat stiffen the batting to facilitate its insertion in the sleeve.

The upper end of core 17 abuts pedestal 13 of the headpiece, whereas the lower end thereof is received within a cylindrical, non-permeable socket 19 of rigid plastic material whose outer diameter is close to the inner diameter of the sleeve so that it may be telescoped therein. Socket 19 is provided at the center of its base with a projecting plug 20 having a bore 20A therein which communicates with the interior of the socket. Extending axially from the bore and attached to the plug is a plastic dip tube 21.

Plug 20 is inserted as a stopper into the cylindrical small diameter mouth 22 of a squeeze bottle 23 formed of flexible plastic material, such as polyethylene or polypropylene, the outer diameter of the bottle being close to the inner diameter of the sleeve. Bottle 23, which contains a reserve supply 24 of a selected liquid fragrance, is placed so that its bottom abuts pedestal 25 of the footpiece 16. The choice of fragrance is a matter of personal preference, taking into account the fact that scents suitable for women's apparel are usually different from those appropriate to male clothing.

In practice, the sleeve may have a length of about 18 inches, with an outer diameter of about an inch, the socket 19 having a length about 1-1/1 inches and bottle 23 a length of about 1¼ inches, the bottle mouth having a length of about ⅜ of an inch. These dimensions are one example of an actual embodiment of the sachet which, in practice, may be longer or shorter than this example.

Dip tube 21 has a length sufficient to cause its free end to reach to a point adjacent the bottom of the bottle. Thus when the sachet is held in a vertical position, and the lower end of the sleeve surrounding the bottle is squeezed, the resultant internal pressure forces the liquid fragrance up dip tube 21 to eject the liquid into the lower end of core 17.

The entire body of the core is initially impregnated with a charge of liquid fragrance so that as the liquid gradually evaporates, the resultant vapor passes into the atmosphere through the pores of the fabric sleeve to scent clothing in the closet or drawer in which the sachet is placed. The sachet, because of its decorative appearance, is not limited to concealed use in closets and drawers, for it may be placed on a table or elsewhere in the living room as a decorative object which exudes a pleasant scent. And with appropriate liquids, it may be used as an air freshener.

When the initial charge is dissipated, the sachet may be recharged by squeezing the bottle end thereof to squirt reserve liquid fragrance into the core end. Because this core end is shielded by cylindrical socket 19 which is impermeable, even though the core end then becomes heavily impregnated with the liquid, no liquid is permitted to escape from this end because of the surrounding shield.

The liquid injected into the core end is thereafter absorbed by the portion of the core which is beyond the shield, the liquid being wicked by the absorbent core material so that it permeates the entire body of the core, thereby recharging the core and prolonging the useful life of the sachet.

As shown in FIG. 5, the dip tube arrangement is such as to minimize leakage of liquid fragrance from bottle 23 when the bottle occupies a horizontal position or a position more horizontal than vertical as is usually the case when the sachet is placed in a drawer or closet. In the horizontal position, the liquid fragrance, particularly when the bottle is partially filled, forms a bath in the bottle whose surface is below the level of the dip tube 21; hence no liquid can flow into the dip tube. However, when the bottle is to be squeezed, the sachet is put in a vertical position so that the dip tube is then immersed in the liquid and the internal pressure resulting from a squeezing action will force the liquid up the tube.

As shown in FIG. 2, the snake-like form of the sachet makes it possible to knot it about a rod or post 26, or, as shown in FIG. 3, to coil the sachet about this post. In a clothes closet, there is usually a horizontal rod to support the clothes hangers, and this rod may also be used to carry the sachet. With a conventional bag-type sachet, one usually places the sachet on a shelf in the closet, and this is not in close proximity to the clothing; hence it is not as effective as a sachet secured to a rod from which the clothing is suspended. The head and tail pieces serve as handles to facilitate knotting or coiling of the sachet.

In placing the sachet in a drawer containing articles of apparel, because the sachet can be made to assume any desired shape, it can be shaped to occupy whatever free space is available in the drawer.

While there has been shown and described a preferred embodiment of a rechargeable sachet in accordance with the invention, it will be appreciated that many changes and modifictions may be made therein without, however, departing from the essential spirit thereof.

I claim:

1. A rechargeable sachet in a snake-like form so that it may be coiled about or otherwise applied to a mounting post, said sachet comprising:
   A. an elongated sleeve of permeable, flexible fabric material having a predetermined length;
   B. a cylindrical flexible core of absorbent material having good wicking properties stuffed in said sleeve, said core being shorter than said sleeve to define a free space therein;
   C. a small squeezable bottle disposed in said free space and containing a supply of a liquid fragrance; and
   D. means intercoupling said bottle and the adjacent end of the core to inject said liquid therein only when the sleeve is manually compressed to squeeze the bottle to produce an internal pressure therein.

2. A rechargeable sachet which emits a scent, said sachet comprising:
   A. a flexible permeable envelope formed of an elongated fabric sleeve having a predetermined length;

B. a cylindrical flexible core of absorbent material having wicking properties stuffed in said sleeve, said core being shorter than said sleeve to define a free space at one end of the sleeve;

C. a relatively small, squeezable bottle disposed in said free space and containing a reserve supply of a liquid fragrance; and D. means intercoupling said bottle and an adajacent end of said core to inject said reserve liquid fragrance into said core only when the envelope is manually compressed to squeeze the bottle to produce an internal pressure therein, said core being initially impregnated with a charge of said liquid fragrance whereby when the initial charge is dissipated by evaporation from said core, the core can then be recharged by a squeezing action to prolong the effective life of the sachet, said means being constituted by a cylindrical shielding socket which receives said corresponding end of the core, said socket having a plug projecting from the base thereof and having a bore therein from which is extended a dip tube, said plug being inserted in the mouth of the bottle, whereby said dip tube is immersed in said reserve liquid fragrance.

3. A sachet as set forth in claim 2, wherein said sleeve is fabricated of velveteen.

4. A sachet as set forth in claim 2, wherein said core is formed of cotton batting.

5. A sachet as set forth in claim 4, wherein said cotton batting is confined within an open-mesh net to form said core which is receivable in said sleeve.

6. A sachet as set forth in claim 2, further including a decorative headpiece secured to an upper end of the sleeve.

7. A sachet as set forth in claim 6, further including a decorative tail piece secured to a lower end of said sleeve.

8. A sachet as set forth in claim 7, wherein said headpiece is formed of an enlarged head section, a constricted neck section and a circular pedestal whose diameter is close to that of the sleeve, whereby the sleeve may be tied to the neck section to expose only the head section.

* * * * *